United States Patent
Wong

[11] Patent Number: 5,794,296
[45] Date of Patent: Aug. 18, 1998

[54] ELECTRIC TOOTHBRUSH

[75] Inventor: Tit Shing Wong, Kowloon, Hong Kong

[73] Assignee: Vontechs Limited, Inc., Hong Kong

[21] Appl. No.: 645,643

[22] Filed: May 16, 1996

[51] Int. Cl.[6] ............................................. A46B 13/02
[52] U.S. Cl. ................................... 15/23; 15/22.1
[58] Field of Search ........................... 15/22.1, 23, 24, 15/28, 29

[56] References Cited

U.S. PATENT DOCUMENTS

| | | |
|---|---|---|
| 2,279,982 | 3/1942 | Glynn . |
| 2,310,626 | 2/1943 | Gold ................................ 15/23 |
| 3,512,201 | 5/1970 | Taylor . |
| 3,661,018 | 5/1972 | Keefer et al. . |
| 3,739,416 | 6/1973 | Kurachi ........................... 15/23 |
| 3,829,922 | 8/1974 | Koblanski . |
| 4,149,291 | 4/1979 | Stoltz . |
| 4,225,994 | 10/1980 | Stoltz . |
| 4,335,480 | 6/1982 | Liu . |
| 4,397,055 | 8/1983 | Cuchiara . |
| 4,709,438 | 12/1987 | De Tavares ...................... 15/23 |
| 4,845,796 | 7/1989 | Mosley . |
| 4,882,801 | 11/1989 | Benz ................................ 15/23 |

FOREIGN PATENT DOCUMENTS 0 240 469 A2  10/1987  European Pat. Off. .

Primary Examiner—Terrence Till
Attorney, Agent, or Firm—Lewis Anten, Esq.; Amedeo Ferraro, Esq.

[57] ABSTRACT

An electric toothbrush is disclosed having a power driven rotary brush in which the direction of rotation of the brush is automatically controlled depending on whether the top or the bottom teeth are being brushed in order to brush any food debris present on the teeth and gums in a direction away from the gums. The toothbrush of the present invention utilizes a direction controller that is placed inside the mouth between the top and bottom teeth. The direction controller controls the direction of brush rotation and serves to stabilize the toothbrush relative to the teeth during the brushing operation. The movement of the direction controller operates a reversing switch to change the direction of rotation of the brush as required to brush in a direction away from the gums and towards the teeth without removing the toothbrush from the mouth.

26 Claims, 2 Drawing Sheets

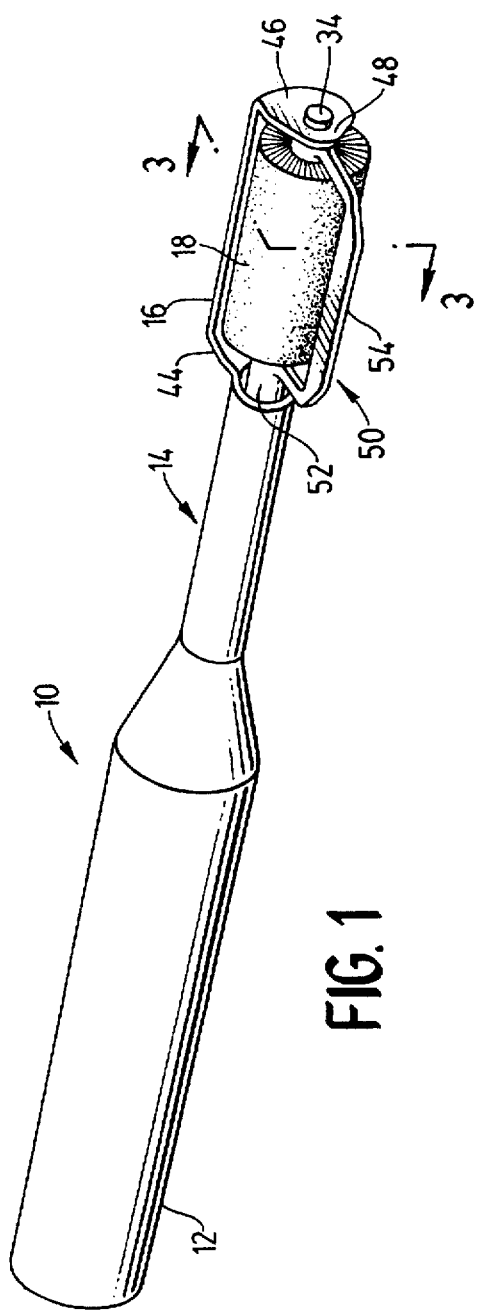
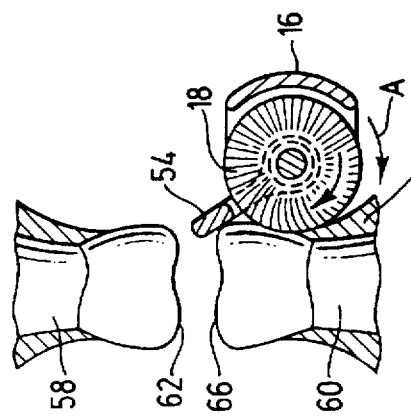
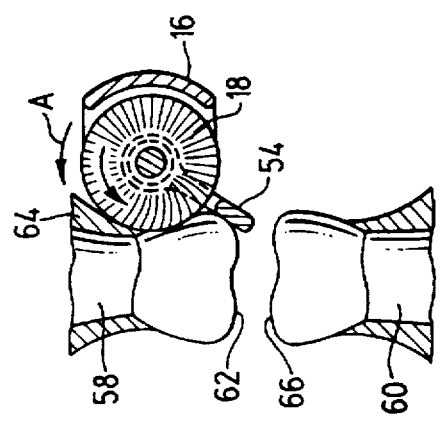
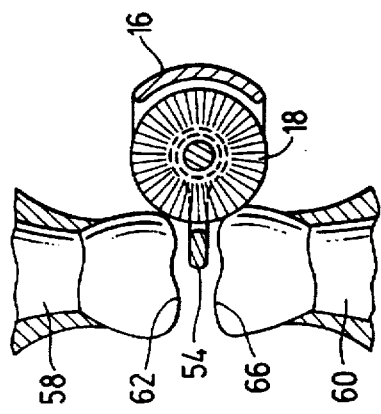

ELECTRIC TOOTHBRUSH

BACKGROUND OF THE INVENTION

1. Field of the Invention

The present invention relates generally to electric toothbrushes and more particularly to a toothbrush having a power driven rotary brush in which the direction of rotation of the brush is automatically controlled depending on whether the top or the bottom teeth are being brushed in order to brush any food debris present on the teeth and gums in a direction away from the gums.

2. Description of the Related Art

According to dentists, the proper way to brush one's teeth is to press a tooth brush with the bristle side resting on the gums and then moving the brush in a direction away from gums and onto teeth. In this manner, any food residue or debris that is present on the teeth and gums will be moved away from the gums. If the brush movement is reversed, i.e. in the direction from the teeth to the gums, the food residue or debris will be forced into the gap that exists between the gums and teeth, resulting in the formation of unwanted plaque.

Most of the electric toothbrushes that are presently in use have a bristle part which is reciprocated through a short arc about the longitudinal axis of the toothbrush. Such a reciprocating movement is quite effective in cleaning some areas of the teeth, but the reciprocating movement is not suitable for cleaning other areas, such as the area near the gumline and the area of the gums adjacent to the cheek. A rotary brush is recognized as being a better cleaner than a reciprocating brush, but the rotary brush also has a number of disadvantages which detract from its suitability for use as a toothbrush. For example, a rotary brush when rotated in one direction only, has a tendency to drive food particles and debris between the teeth the gumline when the brush is rotating in a direction towards the gums.

Attempts have been made in the past to create a motorized rotary toothbrush to control the direction of rotation of the brush. However, all such devices utilize a switching device that is operated by the users' fingers or hands outside of the mouth.

For example, U.S. Pat. No. 2,279,982 to Glynn discloses a toothbrush in which the user has to put the edge of guard (6) against the gums to control the rotation of the brush in a direction away from gums to teeth. The user controls the switching of the brush rotation by pressing the guard (6) against the gums by turning the handle which is located outside of the mouth. If the handle is turned in the wrong direction by the user, until the guard (6) touches any other object, such as the crown of a tooth, the brush will brush in the wrong direction from the tooth towards the gums. Moreover, since the guard (6) of the Glynn toothbrush rests against the gums it is inherently unstable due to the slippery nature of the gums. No means is taught in Glynn for keeping the toothbrush stable during the brushing of the teeth.

U.S. Pat. No. 3,512,201 to Taylor discloses a motorized toothbrush having reciprocal and rotary motion in which the direction of brush rotation is determined by turning the cap of the brush with the thumb and index finger outside of the mouth.

U.S. Pat. No. 3,661,018 to Keefer et al. discloses an electric toothbrush in which the direction of brush rotation is determined by sliding a three-position switch (47) mounted on the brush handle outside of the mouth and is controlled by the user's finger.

U.S. Pat. No. 3,829,922 to Koblansky discloses an electric toothbrush in which the switching of the direction of brush rotation is activated by the movement of guard (46) which is at all times spring-loaded to one position as shown in FIGS. 3 and 6 of the patent. When the guard (46) is at its normal resting position, the toothbrush of Koblansky will always turn in one predetermined direction. Movement of guard (46) by touching a part of the mouth, such as the cheek or gums, causes the reversal of the brush rotation. However, since the guard (46) is spring-loaded such that without any outside force it will always return to its loaded, natural position, it is possible for the brush of Koblansky to rotate in an undesired direction such as away from the teeth and toward the gumline. Moreover, there is no teaching in Koblansky for keeping the toothbrush stable during the brushing of the teeth.

U.S. Pat. No. 4,149,291 to Stoltz discloses a toothbrush in which the direction of the brushing stroke is controlled by a switch (9) that is mounted on the handle to be finger operated by the user outside of the mouth. To use the Stoltz toothbrush properly the user would require training and runs the risk of brushing in the wrong direction.

U.S. Pat. No. 4,225,994 to Stoltz discloses a toothbrush wherein the direction of brushing is changed by the movement of the handle section relative to the housing of the toothbrush. To use the Stoltz brush properly, the user requires training and runs the risk of brushing the teeth in the wrong directions.

U.S. Pat. No. 4,335,480 to Liu discloses a toothbrush wherein in order to change the direction of brushing, the user must manually activate switch (18) which is mounted on the handle outside of the mouth. To use the Liu brush properly, the user requires training and runs the risk of brushing the teeth in the wrong direction.

U.S. Pat. No. 4,397,055 to Cuchiara discloses a toothbrush wherein in order to change the direction of brushing, the user must manually operate the electrical switch (11) mounted on the exterior of the toothbrush housing located outside of the mouth. To use the Cuchiara brush properly, the user requires training and runs the risk of brushing the teeth in the wrong direction.

U.S. Pat. No. 4,845,796 to Mosley discloses a toothbrush wherein in order to control the direction of brushing the user must manually control switches (32) mounted on the handle outside of the mouth. To use the Mosley toothbrush properly, the user requires training and runs the risk of brushing in the wrong direction.

Therefore, there is a need for a motorized toothbrush having a rotating brush in which the direction of brush rotation is controlled automatically depending on whether the upper or lower teeth are being brushed.

SUMMARY OF THE PRESENT INVENTION

The toothbrush of the present invention overcomes the disadvantages of conventional motorized toothbrushes by providing a power driven rotary brush in which the direction of rotation of the brush is automatically controlled depending on whether the top or the bottom teeth are being brushed in order to brush any food debris present on the teeth and gums in a direction away from the gums. The toothbrush of the present invention utilizes a direction controller that is placed inside the mouth between the top and bottom teeth. The direction controller controls the direction of brush rotation and serves to stabilize the toothbrush relative to the teeth during the brushing operation. The movement of the direction controller operates a reversing switch to change the direction of rotation of the rotary brush as required to brush in a direction away from the gums and towards the teeth. It is not necessary to remove the toothbrush from the mouth in order to change the direction of rotation and the cleaning action is substantially continuous once the toothbrush has been inserted in the mouth.

The position of the direction controller relative to the teeth is changed by movement of the toothbrush within the mouth to brush the upper teeth or lower teeth. The switching is "automatic" without the need of manually operating a switch. The rotation of the brush may be controlled by a bi-directional motor having a switching mechanism to change the direction of rotation. Such a switch is activated by the movement of the direction controller. Alternatively, it is appreciated that a single direction motor may be used to rotate the brush and a gearing assembly having a reverse gear may be used to alter direction of the rotation of the brush. The movement of the direction controller can shift the gears directly to change the direction of brush rotation.

During use of the toothbrush of the present invention, the user puts the toothbrush into the user's mouth with the direction controller placed between the upper teeth and lower teeth. When the user pushes the toothbrush upwards toward the roof of the mouth, keeping the direction controller between teeth, the brush rotates in the direction from the gums to the teeth. When the user wants to brush the lower teeth, the brush is lowered toward the lower teeth, keeping the direction controller between the teeth. The rotation of the brush stops when the direction controller is in a horizontal position between upper and lower teeth. To brush the crown of teeth, the controller can either be placed towards the cheek or placed inside the mouth cavity.

BRIEF DESCRIPTION OF THE DRAWINGS

FIG. 1 is a side perspective view of an electric toothbrush in accordance with the present invention.

FIG. 3 is a sectional view taken along the line 3—3 of FIG. 1 of the rotary brush of the electric toothbrush of the present invention shown in place next to the teeth of a patient with the direction controller in the neutral position and the rotary brush in the resting position.

FIG. 4 is a sectional view taken along the line 3—3 of FIG. 1 of the rotary brush of the electric toothbrush of the present invention shown in use with the teeth of a patient with the direction controller in the operating position to clean the upper teeth of a patient with the rotary brush rotating in the direction of arrow A.

FIG. 5 is a sectional view taken along the line 3—3 of FIG. 1 of the rotary brush of the electric toothbrush of the present invention shown in use with the teeth of a patient with the direction controller in the operating position to clean the lower teeth of a patient with the rotary brush rotating in the direction of arrow A.

DETAILED DESCRIPTION OF THE DRAWINGS

Figure 2A:
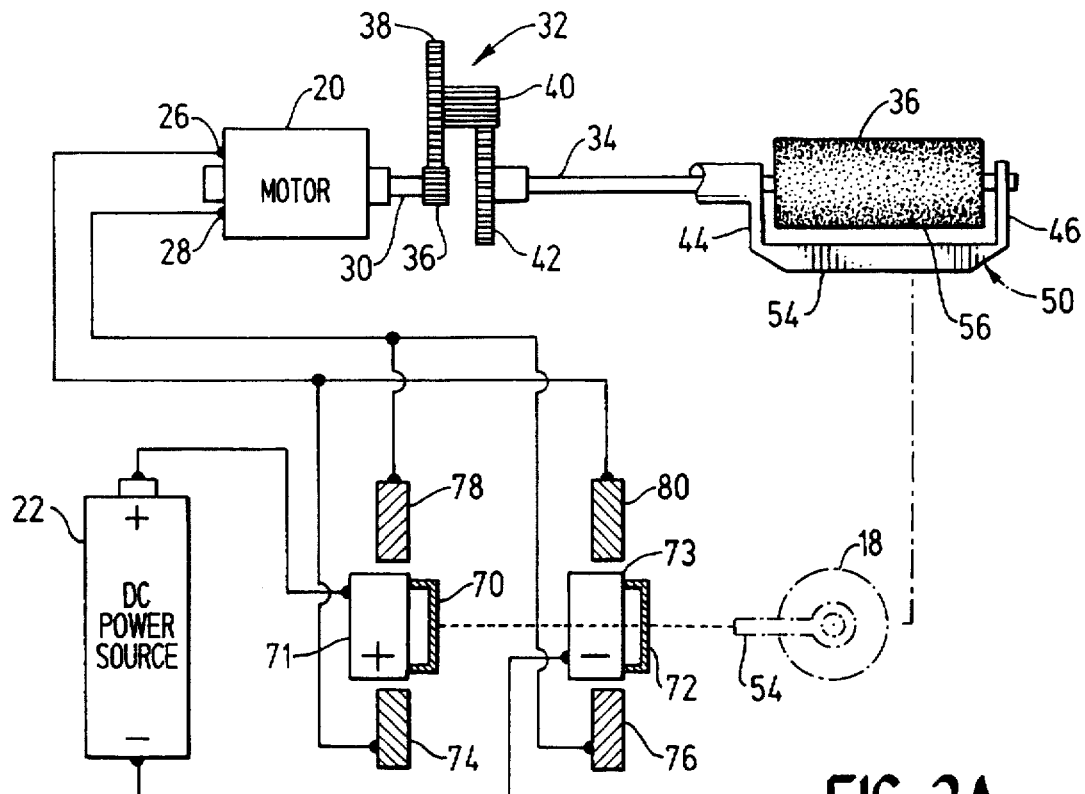
FIG. 2A is a schematic diagram illustrating the electrical components, motor, and gear assembly for the electric toothbrush of the present invention with the direction controller in a horizontal neutral position and the rotary brush in the resting position.

The following description includes the best mode presently contemplated for carrying out the invention. This description is not to be taken in a limiting sense, but is made merely for the purpose of describing the general principles of the invention. The scope of the invention should be determined with reference to the claims.

Referring to FIG. 1, there is shown an electric toothbrush 10 consisting of handle 12, stem 14, brush guard 16 and rotary brush 18. Handle 12 and stem 14 preferably are formed into an integral unit made of durable molded plastic. The electric toothbrush 10 may be sectioned into half units and held together, after insertion of internal parts, by conventional snap fit locking arrangements and the like known in the art. Handle 12 contains a reversible electrical motor 20 (see FIG. 2A) powered by electrical energy source 22. The electrical energy source 22 may be a replaceable or re-chargeable battery, however it must be understood that it is within the contemplation of this invention that the electrical energy source 22 may be a rectified alternating current power source such as conventional 120 v, 60 hz residential power. The power may be brought to the electric tooth brush 10 by way of an electrical cable connected to a conventional wall socket and rectified using conventional circuitry known in the art.

Figure 2B:
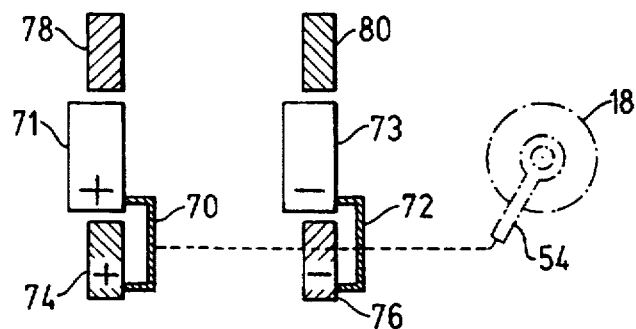
FIG. 2B is a schematic diagram illustrating the interaction between the direction controller and the reversing switch of the electric toothbrush of the present invention with the rotary brush shown in the operation position for cleaning the upper teeth of a person.
Figure 2C:
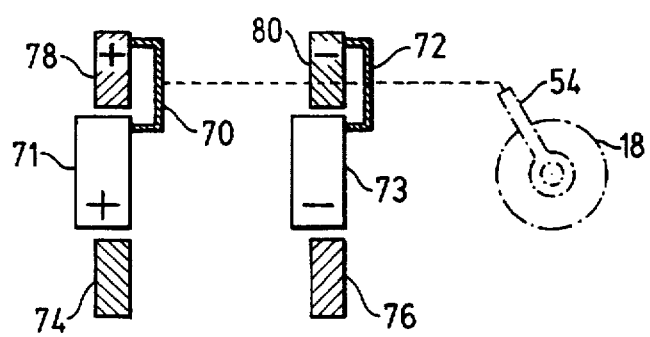
FIG. 2C is a schematic diagram illustrating the interaction between the direction controller and the reversing switch of the electric toothbrush of the present invention with the rotary brush shown in the operation position for cleaning the lower teeth of a person.

The electrical energy source 22 is electrically coupled to motor 20 through reversing switch 24. To be further described later, the reversing switch 24 may assume three independent positions namely: a neutral switch position as shown in FIG. 2A, where the motor 20 is electrically decoupled from the electrical energy source 22; a first switch position as shown in FIG. 2B, where the positive terminal (+) and the negative terminal (−) of energy source 22 are electrically coupled to motor terminals 26 and 28 respectively, to cause the motor 20 to rotate in a first rotational direction; and a second switch position as shown in FIG. 2C, where the positive terminal (+) and the negative terminal (−) of electrical energy source 22 are electrically coupled to motor terminals 28 and 26 respectively, to cause the motor 20 to rotate in a second rotational direction opposite to the first rotational direction.

As shown in schematic form in FIG. 2A, a gear assembly 32 transfers rotation and torque from the motor shaft 30 to rotary brush drive shaft 34 (hereinafter shaft 34). Gear assembly 32 functions as a reducing gear and comprises gears 36, 38, 40 and 42 in a straight tooth spur gear arrangement. Gear 36 mounted on motor shaft 30 engages gear 38 which in turn engages gear 40 which in turn engages gear 42 that is mounted on shaft 34 by any one of conventional techniques. The diameter ratios of gears 36 and 38, and gears 42 and 40 are preferably in the range of 3:1, thereby providing an overall rotational speed reduction from motor shaft 30 to shaft 34 of 9:1, with a corresponding increase in torque from motor shaft 30 to shaft 34 of 9:1. In this manner high speed low torque motors may be advantageously geared down to provide adequate torque for proper low power operation of the electric toothbrush 10. It is to be understood that other gear ratios and gearing configurations may be suitable to achieve low power high torque operation.

As noted in FIG. 1, rotary toothbrush 18, which is located within brush guard 16, is mounted on shaft 34. Brush 18 is generally cylindrically shaped and extends between brush guard ends 44 and 46. The brush guard 16 is partially open so as to partially surround the brush 18 thereby exposing sufficient brush surface for proper engagement with teeth to be cleaned. The brush guard 16 serves to prevent the brush 18 from contacting the inner cheek of the mouth when the electric toothbrush 10 is oriented in the mouth for cleaning teeth. Brush 18 may be fixedly mounted on shaft 34, preferably by a press fit or by keying techniques known in the art.

Brush guard edge 46 also serves as an alignment bearing surface having an annular bearing surface 48 through which shaft 34 extends so as to provide support for brush 18 as it is urged against teeth to be cleaned. The shaft 34 is journaled in the bearing surface 48 and thereby maintains rotation of brush 18 about a fixed axis of rotation defined by shaft 34.

A direction controller 50 is rotatably mounted over shaft 34 between brush guard edge 46 and reversing switch 24. Direction controller 50 includes a hollow essentially cylindrical portion 52 through which shaft 34 extends. The distal end of direction controller 50 may be mounted on guard edge 46 using any one of known techniques. For example, the inward facing surface of guard edge 46 may include a protruding annular shoulder for seating a mating annular recess in the distal end of the direction controller 50 in a rotational slip fit arrangement. The cylindrical portion 52 extends through stem 14 and is mounted at its proximal end to reversing switch 24. The direction controller 50 includes a ledge 54 which extends in close proximity along the length of brush outer edge 56. The ledge 54 is designed to fit between the upper and lower teeth of a person and makes contact with the crowns 62, 66 of the teeth. The contact of the ledge 54 with the crowns 62, 66 cause the ledge 54 to be urged in a clockwise or counterclockwise direction, respectively. In addition to controlling the direction of the brush rotation, the ledge 54 functions to stabilize the brush 18 relative to the teeth, as the ledge 54 is held in place between the crowns 62, 66 of the top and bottom teeth of the user. Switch 24 provides a slight resistance to movement such that ledge 54 remains fixed in position unless urged in either a clockwise or counter clockwise rotation as the case may be. With reference to FIGS. 3, 4, and 5, movement of the direction controller 50 may be appreciated. As shown in FIG. 3, the ledge 54, while in the neutral position, extends horizontally between the crowns 62 of upper teeth 58 and the crowns 66 of lower teeth 60. In such position the reversing switch 24 electrically disconnects the motor 20 from the energy source 22. Accordingly, motor 20 is de-energized and brush 18 does not rotate.

As shown in FIG. 4, the electric toothbrush 10 is moved upward, relative to the neutral position, when it is desired to brush upper teeth 58. In doing so, ledge 54 contacts the crowns 62 of upper teeth 58 thereby urging the ledge 54 in a counter clockwise rotation against the slight resistance of switch 24 placing it in a first position (see FIG. 2B), thereby energizing motor 20 so as to cause brush 18 to rotate in a counter clockwise direction. As shown in FIG. 3, rotation of the brush 18 in a counter clockwise direction causes contaminants to be brushed away from the gums 64, insuring that such contaminants are not brushed under the gums 64 but rather away from the gums.

Similarly and as shown in FIG. 5, the electric toothbrush 10 is moved downward, relative to the neutral position, when it is desired to brush lower teeth 60. In doing so ledge 54 contacts the crowns 66 of lower teeth 60 thereby urging the ledge 54 in a clockwise rotation to place switch 24 in a second position (see FIG. 2C), thereby causing motor 20 to be energized so as to cause brush 18 to rotate in a clockwise direction. In doing so contaminants are brushed away from gums 68 insuring that such contaminants are not brushed under gums 68. Although not shown, it should be appreciated that when brushing teeth 58 and 60, brush guard 16 prevents brush 18 from contacting the inner cheek portion of the mouth. Thus, the ledge 54 provides the necessary feed back to the electric toothbrush 10 to control the direction of rotation of the brush 18.

Turning now to FIGS. 2A–C, the interaction between the direction controller 50 and switch 24, to control the direction of rotation of motor 10, may be understood. More specifically, as shown in FIG. 2A, the ledge 54 is shown in the neutral cylindrical position. The direction controller cylindrical portion 52 is coupled (shown in dotted lines) to a pair of electrical contacts 70 and 72. In such position contacts 70 and 72 are restricted to making electrical contact with contact pads 71 and 73 respectively, (contact pads 71 and 73 are coupled to energy source positive terminal (+) and the negative terminal (−) respectively). In such position an open circuit exists between energy source 22 and motor 20 and motor 20 remains de-energized.

As previously described when the electric toothbrush 10 is moved upward to brush upper teeth 58, the ledge 54 moves in a counter clockwise direction thereby bringing electrical contacts 70 and 72 into electrical contact with contact pads 74 and 76 respectively. Accordingly, the energy source positive terminal (+) is electrically coupled to motor terminal 26 through an electrical path that includes contact pad 71, electrical contact 70 and contact pad 74. Similarly the energy source negative terminal (−) is electrically coupled to motor terminal 28 through an electrical path that includes contact pad 73, electrical contact 72 and contact pad 76. At this polarity setting motor 20 rotates to cause brush 18 to rotate in a counter clockwise direction.

Similarly when the electric toothbrush 10 is moved downward to brush lower teeth 60, the ledge 54 moves in a clockwise direction thereby bringing electrical contacts 70 and 72 into electrical contact with contact pads 78 and 80, respectively. Accordingly, the energy source positive terminal (+) is electrically coupled to motor terminal 28 through an electrical path that includes contact pad 71, electrical contact 71 and contact pad 78. Similarly, the energy source negative terminal (−) is electrically coupled to motor terminal 26 through an electrical path that includes contact pad 73, electrical contact 72 and contact pad 80. At this polarity setting the motor 20 rotates to cause the brush 18 to rotate in a clockwise direction. Preferably, the electrical contacts and contact pads may be constructed of or coated with a non-corrosive metal so as to withstand arcing.

As an alternative to the embodiment of the electric toothbrush described above, the reversing switch 24 may comprise an external magnet that is linked to the direction controller 50 used to activate the motor 20. In this alternative embodiment, the external magnet rides on the surface of the handle 12 and two magnetic-reed switches are placed inside the handle 12. The magnetic-reed switches are oriented inside the handle 12 such that when the direction controller 50 moves the external magnet to the proximity of one magnetic-reed switch, the motor 20 turns in one direction. When the direction controller 50 moves the external magnet to the proximity of the other magnetic-reed switch, the motor 20 turns in the other direction. When the external magnet is oriented between the two magnetic-reed switches, none of the magnetic switches is activated and the motor 20 stops. The use of an external magnet on the surface of the handle 12 enhances the water-proofing of the electric toothbrush 10 as the magnetic-reed switches may be sealed within the handle 12.

It is appreciated that instead of utilizing a bi-directional motor, the motor 50 may be unidirectional and the direction of brush rotation may be altered by a gear assembly having forward and reverse gears known in the art. The engagement of the reverse gear of such a gear assembly would be controlled by the position of the direction controller 50. For example, the position of the direction controller 50 can be used to shift the reverse and forward gears of the gear train inside the handle to change the brush's direction of rotation.

While the invention herein has been described by means of specific embodiments, numerous modifications and variations could be made thereto by those skilled in the art without departing from the scope of the invention set forth in the claims.

What is claimed is:

1. An electric toothbrush comprising:

a housing;

a bi-directional electric motor mounted within the housing, the motor having a motor shaft axially disposed within the housing, the direction of rotation of the shaft being dependent upon the polarity of electrical energy supplied to the motor;

a source of electrical energy contained within the housing;

a multi-position electrical reversing switch electrically coupled between the motor and the source of electrical energy, the reversing switch adapted for reversing the polarity of electrical energy supplied to the motor such that when the reversing switch is in a first position the motor shaft rotates in a first direction and when the reversing switch is in a second position the motor shaft rotates in a second direction opposite to the first direction, said reversing switch having a neutral position wherein the motor is electrically disconnected from the source of electrical energy;

a rotary brush rotatably mounted at a distal end of the housing, the brush being mechanically coupled to the motor shaft; and a direction controller coupled to the reversing switch, the controller moveable between at least first and second positions there by moving the reversing switch between first and second positions, respectively, the controller disposed adjacent the rotary brush such that when the electric tooth brush is brought into proximity with upper teeth to be cleaned the controller is brought into contact with the crowns of such upper teeth and is thereby moved to a first position to cause rotation of the motor shaft in a first direction and when the electric tooth brush is brought into proximity with lower teeth to be cleaned the controller is brought into contact with the crowns of such lower teeth and is thereby moved to the second position to cause rotation of the motor shaft in the second direction, said controller having a neutral position such that when the controller is moved to the neutral position the motor is thereby de-energized.

2. The electric toothbrush of claim 1 wherein the housing comprises a brush guard in proximity to and partially surrounding the rotary brush to prevent the rotary brush from contacting an inner region of the mouth when the electric toothbrush is inserted in the mouth and oriented for cleaning teeth.

3. The electric toothbrush of claim 2 wherein the brush guard includes an alignment bearing surface to provide rotational support for the rotary brush and for maintaining rotation of the rotary brush about a fixed axis of rotation.

4. The electric toothbrush of claim 1 further comprising a gear assembly coupled between the motor shaft and the rotary brush, the gear assembly having a gear ratio for reducing the rotational speed and increasing the torque of the rotary brush relative to the motor shaft.

5. An electric toothbrush comprising:

a handle;

a reversible motor mounted within the handle;

a brush guard and stem housing extending from the handle;

a rotary brush drive shaft mounted within the brush guard and stem housing and rotatable about an axis of rotation, the rotary brush drive shaft connected at one end thereof to the motor;

a rotary brush mounted at the other end of the rotary brush drive shaft for rotation about the axis of rotation; and a moveable direction controller disposed adjacent the rotary brush, the direction controller electrically coupled to the motor and adapted for reversing the rotation of the motor, the direction controller having a ledge portion adapted for contact with a crown portion of teeth so that when in use and the ledge portion is urged against the crown portion of upper teeth the brush rotates in a first direction and when the ledge portion is urged against the crown portion of lower teeth the brush rotates in a second direction opposite to the first direction.

6. The electric toothbrush of claim 5 wherein the brush guard and stem housing comprises an alignment bearing surface and the rotary brush drive shaft is journaled in the bearing surface to provide rotational support for the rotary brush and to maintain rotation of the rotary brush about the axis of rotation.

7. The electric toothbrush of claim 5 further comprising a gear assembly coupled between the motor and the rotary brush drive shaft.

8. The electric toothbrush of claim 7 wherein the gear assembly comprises a gear arrangement for reducing the speed and increasing the torque of the rotary brush drive shaft relative to the motor.

9. The electric toothbrush of claim 8 wherein the direction controller extends within the brush guard and stem housing between the brush guard and the motor, the direction controller having a hollow portion for receiving the rotary brush drive shaft which extends therethrough.

10. An electric toothbrush comprising:

a handle;

a bi-directional electrical motor mounted within the handle;

electrical energy means for energizing the motor;

switch means for reversibly coupling the motor to the electrical energy means;

drive shaft means coupled to the motor;

rotary brush means coupled to the drive shaft means for rotation about an axis of rotation; and direction means coupled to the switch means for controlling the direction of rotation of the motor and therefore the rotation of the rotary brush means, the direction means having a ledge for contacting upper and lower teeth such that when the direction means is urged against upper teeth, rotation of the rotary brush means is in a first direction and when the direction means is urged against lower teeth, rotation of the rotary brush means is in a second direction.

11. The electric toothbrush of claim 10 comprising gear means coupled between the drive shaft means and the motor for decreasing the speed and increasing the torque of the drive shaft means relative to the motor.

12. An electric toothbrush comprising:

a handle;

a motor mounted within the handle;

a brush guard and stem housing extending from the handle;

a rotary brush drive shaft mounted within the brush guard and stem housing and rotatable about an axis of rotation, the rotary brush drive shaft coupled to the motor;

a direction changing means for changing the direction of rotation of the rotary brush drive shaft;

a rotary brush mounted at the other end of the rotary brush drive shaft for rotation about the axis of rotation; and a moveable direction controller disposed adjacent the rotary brush, the direction controller coupled to the direction changing means and adapted for reversing the rotation of the motor, the direction controller having a ledge portion adapted for contact with a crown portion of the teeth so that when in use and the ledge portion is urged against the crown portion of upper teeth the brush rotates in a first direction and when the ledge portion is urged against the crown portion of lower teeth the brush rotates in a second direction opposite to the first direction.

13. The electric toothbrush of claim 12 wherein the brush guard and stem housing comprises an alignment bearing surface and the rotary brush drive shaft is journaled in the bearing surface to provide rotational support for the rotary brush and to maintain rotation of the rotary brush about the axis of rotation.

14. The electric toothbrush of claim 12 further comprising a gear assembly coupled between the motor and the rotary brush drive shaft.

15. The electric toothbrush of claim 14 wherein the gear assembly comprises a gear arrangement for reducing the speed and increasing the torque of the rotary brush drive shaft relative to the motor.

16. The electric toothbrush of claim 15 wherein the direction controller extends within the brush guard and stem housing between the brush guard and the motor, the direction controller having a hollow portion for receiving the rotary brush drive shaft which extends therethrough.

17. The electric toothbrush of claim 12 in which said direction changing means comprises reverse gear for reversing the direction of rotation of the rotary brush drive shaft.

18. The electric toothbrush of claim 17 in which said direction changing means is activated by the movement of said direction controller.

19. An electric toothbrush comprising:

a handle;

a bi-directional electrical motor mounted within the handle;

electrical energy means for energizing the motor;

a three position switch means for reversibly coupling the motor to the electrical energy means;

drive shaft means coupled to the motor;

rotary brush means coupled to the drive shaft means for rotation about an axis of rotation; and direction means for controlling the direction of rotation of the motor coupled to said switch means, said direction means disposed proximate said rotary brush means and rotatable about the axis of rotation of said rotary brush means to activate the switch means for controlling the direction of rotation of the motor and therefor the direction of rotation of the rotary brush means.

20. The electric toothbrush of claim 19 wherein the direction means is further for contacting upper and lower teeth such that when the direction means is urged against upper teeth, rotation of the rotary brush is in a first direction and when the direction means is urged against lower teeth, rotation of the rotary brush means is in a second direction.

21. The electric toothbrush of claim 19 wherein the reversing switch further includes a neutral position wherein the motor is electrically disconnected from the source of electrical energy and wherein the controller includes a neutral position such that when the controller is moved to the neutral position the motor is thereby de-energized.

22. The electric toothbrush of claim 19 wherein the housing comprises a brush guard in proximity to and partially surrounding the rotary brush to prevent the rotary brush from contacting an inner region of the mouth when the electric toothbrush is inserted in the mouth and oriented for cleaning teeth.

23. The electric toothbrush of claim 22 wherein the brush guard includes an alignment bearing surface to provide rotational support for the rotary brush and for maintaining rotation of the rotary brush about a fixed axis of rotation.

24. An electric toothbrush comprising:

a handle;

a motor mounted within the handle;

a brush guard and stem housing extending from the handle;

a drive shaft mounted within the brush guard and stem housing and rotatable about an axis of rotation, the drive shaft connected at one end thereof to the motor;

a rotary brush mounted at the other end of the drive shaft for rotation about the axis of rotation;

a switch coupled to the motor, said switch having a neutral position for disconnecting the motor; and a moveable direction controller coupled to the switch and adapted for controlling the rotation of the motor, the controller having a neutral position for placing the switch in the neutral position whereby the motor is disconnected when the controller is in the neutral position.

25. The electric tooth brush of claim 24 wherein the direction controller has a ledge portion adapted for contact with a crown portion of teeth so that when in use and the ledge portion is urged against the crown portion of upper teeth the brush rotates in a first direction and when the ledge portion is urged against the crown portion of lower teeth the brush rotates in a second direction opposite to the first direction.

26. An electric toothbrush comprising:

a handle;

a motor mounted within the handle;

a brush guard and stem housing extending from the handle, the brush guard having an alignment bearing surface to provide rotational support for the rotary brush and for maintaining rotation of the rotary brush about a fixed axis of rotation, said alignment bearing surface including a ledge for contacting the teeth of a user of said toothbrush;

a drive shaft mounted within the brush guard and stem housing and rotatable about an axis of rotation, the drive shaft connected at one end thereof to the motor; and a rotary brush mounted at the other end of the drive shaft for rotation about the axis of rotation.

* * * * *